US006987092B1

(12) United States Patent
Eisenbrand et al.

(10) Patent No.: US 6,987,092 B1
(45) Date of Patent: Jan. 17, 2006

(54) INDIGOID BISINDOLE DERIVATIVES

(75) Inventors: Gerhard Eisenbrand, Heidelberg (DE); Doris Marko, Kaiserslautern (DE); Andrea Thommet, Kaiserslautern (DE); Stefan Schwahn, Worms (DE)

(73) Assignee: Faustus Forschungs Cie. Translational Cancer Research GmbH, Leipzig (DE)

( * ) Notice: Subject to any disclaimer, the term of this patent is extended or adjusted under 35 U.S.C. 154(b) by 0 days.

(21) Appl. No.: 09/958,476

(22) PCT Filed: Apr. 12, 2000

(86) PCT No.: PCT/EP00/03285

§ 371 (c)(1),
(2), (4) Date: Jan. 9, 2002

(87) PCT Pub. No.: WO00/61555

PCT Pub. Date: Oct. 19, 2000

(30) Foreign Application Priority Data

Apr. 12, 1999 (EP) ................... 99106207
Apr. 27, 1999 (EP) ................... 99107429

(51) Int. Cl.
*A61K 31/404* (2006.01)
*A61P 35/00* (2006.01)
*C07D 209/34* (2006.01)

(52) U.S. Cl. ................ 514/25; 514/414; 536/1.11; 548/457

(58) Field of Classification Search ............. 536/1.11; 548/457; 514/25, 414
See application file for complete search history.

(56) References Cited

FOREIGN PATENT DOCUMENTS

| EP | 0 966 963 A1 | 12/1999 |
|---|---|---|
| HU | 198946 B | 4/1990 |
| JP | 57-209271 | 12/1982 |
| JP | 57-209272 | 12/1982 |
| JP | 61-7254 | 1/1986 |
| JP | 03223363 | 10/1991 |
| WO | WO 99/62503 | 12/1999 |

OTHER PUBLICATIONS

Hungarian Search Report dated Sep. 17, 2002 in Hungarian Application No. P0200724/7.
Ralph Hoessel et al., "*Indirubin, the active constituent of a Chinese entileukaemia medicine, inhibits cyclin-dependent kinases,*" Nature Cell Biology, GB, MacMillan Publishers, vol. 1, No. 1, May 1, 1999, pp. 60-67.
Chunmin Li et al., "*The Synthesis, Antileukemic Activity, and Crystal Structures of Indirubin Derivatives,*" Bull. Chem. Soc. JPN., vol. 69, No. 6, 1996, pp. 1621-1627.
Y.C. Gu et al., "*Synthesis of some halogenated indirubin derivatives,*" Chemical Abstract, vol. 112, No. 19, Abstract No. 178548, May 7, 1990, 2 pages.
Ji Xiujuan et al., "*Antineoplastic effect of indirubin derivatives and their structure-activity relations,*" Chemical Abstract, vol. 103, No. 13, Abstract No. 98313, Sep. 30, 1985, 1 page.

*Primary Examiner*—Kamal A. Saeed
(74) *Attorney, Agent, or Firm*—Burns, Doane, Swecker & Mathis, L.L.P.

(57) ABSTRACT

The present invention relates to novel indigoid binsindole derivatives which can be used for the manufacture of a medicament for the treatment of solid cancers.

14 Claims, No Drawings

INDIGOID BISINDOLE DERIVATIVES

The present invention relates to novel indigoid bisindole derivatives which can be used for the manufacture of a medicament for the treatment of solid cancers.

Indigoid bisindoles comprise a spectrum of natural dye stuffs. Many of these can be obtained from plans. Accordingly, indirubin, indigo and isoindigo are natural products which can be obtained from different plants: namely, Baphicacanthus cusia (Acanthaceae), Indigofera suffruticosa (Fabaceae), Isatis indigotica (Brassicaceae) and others. Indican, a glycoside which is found in plants, gives glucose and 3-hydroxyindole due to acidic or enzymatic hydrolysis. 3-Hydroxyindole is converted by air-oxidation into indigo and its isomers. Indigo naturalis (Chinese: Quing Dai) is the natural blue dye obtained from plant material, e.g. Isatis indigotica (Brassicaceae). Indirubin, an isomer of indigo, can be found in Indigo naturalis in an amount of up to 60% (Falbe J. & Regitz M., R mpp Chemie Lexikon (1992), 9. Aufl., Stuttgart, Georg Thieme Verlag). It occurs also in Isatis tinctoria in an amount of up to 5% which is indigenous to Central Europe (Gelius R., Z. Chem., 20, (1980), 340–341). Derivatives of indirubin are known for a long time as dyes of low persistence.

Indigo naturalis is reported to be used in traditional Chinese medicine as a haemostatic, anti-pyretic, anti-inflammatory and sedative agent in the treatment of bacterial and viral infections. Antileukemic effects of Indigo naturalis have also been reported, with indirubin being the effective principle (Ji X. et al., Acta Pharm. Sin., 16, (1981), 146–148; Gan W. J. et al., J. Hematol., 6, (1985), 611–613). In spite of its anti-leukaemic activity, however, indirubin dissolves only poorly in water and is therefore not readily resorbed. Recently, the antileukemic activity of some better soluble indirubin derivatives has been reported (Ch. Li et al., Bull. Chem. Soc. Jpn. 69, 1621–1627,(1996)).

However, indigoid bisindole or its derivatives have never been investigated with respect to solid tumors, in particular human solid tumors, and furthermore, the problem of the poor solubility resulting in a poor resorption has not been sufficiently solved yet.

Thus, the technical problem underlying the present invention is to provide new active substances which can be used in the treatment of human solid tumors and metastases thereof. Furthermore, the resorbability of said substances should be improved in order to improve their in vivo anti-tumor activity.

The solution to the above technical problem is achieved by the embodiments characterized in the claims.

In particular, the present invention relates to cell membrane penetrating indigoid bisindole derivatives selected from indigo derivatives, isoindigo derivatives and indirubin derivatives wherein the indigoid bisindole derivatives are compounds having the general formula (I)

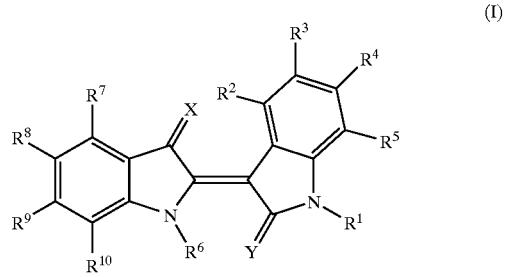

wherein:

X and Y are the same or different and represent an oxygen atom; a sulphur atom; a selenium atom; a tellurium atom; a group N—A—B—$R^{14}$ in which A represents a single bond or an oxygen atom, —NH— or —NH—CO—, B represents a single bond or a group $[(CD_2)_nZ]_m$ wherein D has the same meaning as $R^{14}$ (see below) and Z is an oxygen atom or —NH—, n is 0 or an integer and m is an integer; and the group $R^{14}$ represents a hydrogen atom, a straight-chain or branched-chain alkyl group having 1 to 18 carbon atoms which can carry one or more hydroxy and/or amino groups and can be substituted by one or more carboxyl groups and/or phosphoryl groups, a substituted or unsubstituted aryl group which can comprise one or more heteroatoms, an aralkyl group, an acyl group, a glycoside selected from monosaccharides, disaccharides or oligosaccharides, or a group selected from the group consisting of sugars, amino acids, peptides or steroid hormones; or a hydrazone group N—$NR^{15}R^{16}$, wherein $R^{15}$ and $R^{16}$ can be the same or different and represent a hydrogen atom, a straight-chain or branched-chain alkyl group having 1 to 18 carbon atoms which can be substituted by one or more carboxyl groups and/or phosphoryl groups, a substituted or unsubstituted aryl group which can comprise one or more heteroatoms, an aralkyl group, an acyl group, or a glycoside selected from monosaccharides, disaccharides or oligosaccharides, or a group selected from the group consisting of sugars, amino acids, peptides or steroid hormones;

$R^2$, $R^3$, $R^4$, $R^5$, $R^7$, $R^8$, $R^9$ and $R^{10}$ can be the same or different and represent a hydrogen atom; a halogen atom; a hydroxy group; a nitroso group; a nitro group; an aryloxy group; an alkoxy group; a straight-chain or branched-chain alkyl group having 1 to 18 carbon atoms which can additionally carry one or more hydroxy and/or amino groups; a substituted or unsubstituted aryl group which can comprise one or more heteroatoms; a cycloalkyl group having 3 to 7 carbon atoms which can comprise one or more heteroatoms; an aralkyl group; a trifluoromethyl group; a —COM group; a —COOM group; a —$CH_2$COOM group, wherein M is hydrogen, a straight-chain or branched-chain alkyl group having 1 to 18 carbon atoms which can additionally carry one or more hydroxy and/or amino groups, or an aryl group which can comprise one or more heteroatoms and can be substituted with one or more halogen atoms, one or more alkyl groups or one or more alkoxy groups; a —$NR^{11}R^{12}$ group, wherein $R^{11}$ and $R^{12}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group, or $R^{11}$ and $R^{12}$ form together a ring having 2 to 6, optionally substituted, $CH_2$ groups; a benzyl group, wherein the benzene nucleus can comprise one or more heteroatoms; a hydroxylamino group; a phosphate group; a phosphonate group; a sulfate group; a sulfonamide group, wherein the nitrogen atom can be independently substituted by a hydrogen atom, a straight-chain or branched-chain alkyl group having 1 to 18 carbon atoms which can additionally carry one or more hydroxy and/or amino groups, a substituted or unsubstituted aryl group or wherein the nitrogen atom is part of a cycloalkyl group having 3 to 7 carbon atoms which can comprise one or more heteroatoms; an azo group $N=N-R^{13}$, in which $R^{13}$ represents an aromatic system which can be substituted by one or more carboxyl groups and/or phosphoryl groups; or a O-glycoside or a N-glycoside, wherein the glycoside is selected from monosaccharides, disaccharides or oligosaccharides; or a group selected from the group consisting of sugars, amino acids, peptides or steroid hormones; or $R^1$ and $R^5$, and $R^6$ and $R^{10}$, respectively, form independently from each other a ring together having 1 to 4, optionally substituted, $CH_2$ groups;

the groups $R^1$ and $R^6$ are the same or different and represent a hydrogen atom; a halogen atom; a hydroxy group; a methylenehydroxy group; a straight-chain or branched-chain alkyl group having 1 to 18 carbon atoms; a cycloalkyl group having 3 to 7 carbon atoms which can comprise one or more heteroatoms; a substituted or unsubstituted aryl group which can comprise one or more heteroatoms; a mono-, di- or trialkylsilyl group having 1 to 6 carbon atoms independently of each other in each instance in the straight-chain or branched-chain alkyl group; a mono-, di- or triarylsilyl group with substituted or unsubstituted aryl groups independently of each other in each instance; an aralkyl group; a trifluoromethyl group; a —COM group; a —COOM group; a —CH₂COOM group, wherein M is hydrogen, a straight-chain or branched-chain alkyl group having 1 to 18 carbon atoms which can additionally carry one or more hydroxy and/or amino groups, or an aryl group which can comprise one or more heteroatoms and can be substituted with one or more halogen atoms, one or more alkyl groups or one or more alkoxy groups; a —NR$^{17}$R$^{18}$ group, wherein $R^{17}$ and $R^{18}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group; a methyleneamino group —CH$_2$—NR$^{17}$R$^{18}$, wherein $R^{17}$ and $R^{18}$ have the above definitions; a benzyl group, wherein the benzene nucleus can comprise one or more heteroatoms; a methylenecycloalkyl group having 3 to 7 carbon atoms which can comprise one or more heteroatoms; a physiological amino acid residue bound to the nitrogen as an amide; an O-glycoside or a N-glycoside, wherein the glycoside is selected from monosaccharides, disaccharides or oligosaccharides; or a group selected from the group consisting of sugars, amino acids, peptides or steroid hormones; or a methylene sulfonate group.

The above mentioned sugars can e.g. be connected to the indigiod bisindole derivative as a N-glycoside or an O-glycoside, such as a α/βD-glycoside, and the glycoside is preferably selected from mono-, di- and oligosaccharides.

The above mentioned peptide may be an oligo- or polypeptide and may e.g. be a NH—CO-peptide sequence or a NH—CO-peptide-polymer sequence employed as a typical substrate for tumor associated proteases (e.g. plasmin, cathepsin and collagenases). Such peptide sequences can be e.g. D-Ala-Phen-Lys, D-Val-Leu-Lys or Gly-Phen-Leu-Gly. The number of amino acids within the peptide sequence is preferably 1 to 6 amino acids. In the NH—CO-peptide-polymer sequence the polymer is not limited and e.g. hydroxypropyl methacrylamid copolymers can be used.

The above mentioned steroid hormone can e.g. be selected from glucocorticiods or sex hormones such as androgens, oestrogens and gestagens.

The isoindigo derivative is preferably a compound having the general formula (II)

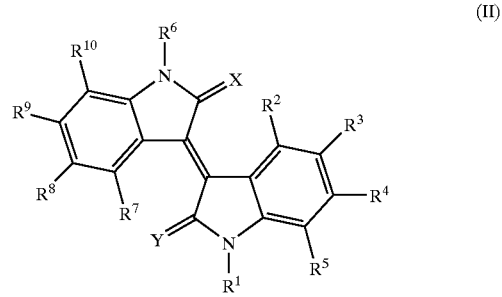

(II)

wherein $R^1$ to $R^{10}$ and X and Y have the meanings as defined above.

Prefereably, the indigo derivative is a compound having the general formula (III)

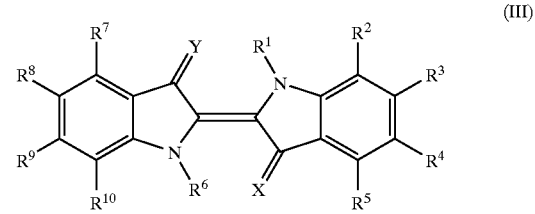

(III)

wherein $R^1$ to $R^{10}$ and X and Y have the meanings as defined above.

According to another embodiment of the present invention, the indigo compound may further be a compound having the general formula (IV):

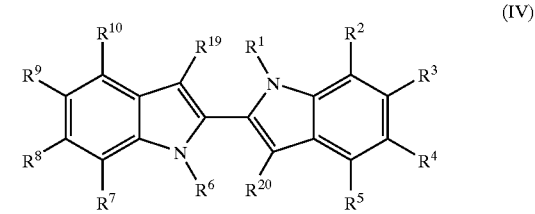

(IV)

wherein $R^1$ to $R^{10}$ have the meaning as defined above and $R^{19}$ and $R^{20}$ which may be the same or different have the same meaning as defined for e.g. $R^2$ above.

In the above indigoid bisindole derivatives having the general formulae (I), (II) and (III), one or more ring atoms of the benzene nuclei may be replaced by nitrogen atoms. Furthermore, the indigoid bisindole derivatives having the general formulae (I), (II) and (III) may according to one embodiment of the present invention be bound to a polyethyleneglycolester or a polyethyleneglycol-ether.

In the above formulae (I), (II) and (III), Y preferably represents an oxygen atom and $R^1$ preferably represents a hydrogen atom.

The indigoid bisindole derivatives according to the present invention may also be chemically coupled to masking agents as described in German patent application DE-A-38 27 488 which function to carry the anti-tumor active substances to the tumor.

In the following, the indigoid bisindole derivatives selected from indigo, isoindigo and indirubin derivatives according to the present invention are also addressed to as "anti-tumor active compounds according to the present invention".

The anti-tumor active compounds according to the present invention can be used for the manufacture of a medicament for the treatment of human solid tumors and metastases thereof. The term "human solid tumors" according to the present invention preferably includes carcinomas, melanomas, adenomas, sarcomas, lymphomas, neuroblastomas, teratomas and astrocytomas. Specific examples are mammary carcinoma, large-cell lung carcinoma, small-cell lung carcinoma, lung adenocarcinoma, colon carcinoma, bladder carcinoma, ovarian carcinoma, pancreatic carcinoma, renal carcinoma, prostatic carcinoma, bronchial carcinoma, laryngeal carcinoma and the like.

One general problem in the field of pharmacology is the formulation of pharmaceutically active substances in pharmaceutical compositions which can be applied to a human body. Since most physiological fluids are water-based, the pharmaceutically active substances should be soluble in water and/or a water mixable solvent wherein the latter of course has to be physiologically acceptable in small concentrations, such as ethanol. Furthermore, pharmaceutically active substances which are taken orally have to be resorbed into surface of the human body including the gastrointestinal mucous membrane or, in case of an application via syringe, e.g. intraperitoneal or intravasal, have to be resorbed through the cellular membranes of the of destination cells, specifically, into the tumor cells.

According to the present invention it has been found that in case of the indigoid bisindole derivatives according to the present invention, a good solubility is not the only prerequisite guaranteeing a good anti-tumor activity in vivo as it will become apparent by the below Examples. An important factor for the anti-tumor activity of indigoid bisindole derivatives is their ability to penetrate the cellular membranes of the tumor cells. Cellular membranes are composed of lipid bilayers, i.e. compose a rather non-polar medium. Therefore, substitution with very polar groups on the one hand improves the water solubility of a compound but on the other hand hinders or even prohibits the resorption of anti-tumor active substances into a tumor cell. Thus, anti-tumor active substances which show good anti-tumor activities under certain in vitro conditions, have to be rejected because of not showing any activity when tested using intact cells or in vivo.

Therefore, the indigoid bisindole derivatives according to the present invention are cell membrane penetrating indigoid bisindoles. According to the present invention the terms "cell membrane penetrating" and "cell resorbable" mean the ability of the indigoid bisindole derivatives to be taken up by the tumor cell through the cellular membrane.

Therefore, according to a prefered embodiment of the present invention, the indigoid bisindole derivatives according to the present invention are selected from substituted indirubine derivatives, substituted isoindigo derivatives and substituted indigo derivatives, i.e. the groups $R^2$ to $R^5$ and $R^7$ to $R^{10}$ in above formulas (I), (II) and (III) do not all represent hydrogen atoms simultaneously. In case of the indirubine derivatives according to above formula (I), the groups $R^2$ to $R^5$ and $R^7$ to $R^{10}$ may all represent hydrogen atoms if the group X represents a group N—A—B—$R^{14}$ wherein A, B and $R^{14}$ have the above defined meaning. Even more preferably, the indirubine derivatives, isoindigo derivatives and indigo derivatives are not substituted with easily dissociating, very polar groups, such as a non-substituted sulfonate group $SO_3H$.

The present invention further relates to a pharmaceutical formulation comprising at least one of the indigoid bisindol derivatives according to the present invention in a pharmaceutically active amount.

In the pharmaceutical formulations according to the present invention, the indigoid bisindole derivatives can also be employed in the form of their physiologically acceptable salts. The above identified indigoid bisindole derivatives of the present invention can be formulated into pharmaceutical compositions which contain optionally a pharmaceutically acceptable carrier and/or diluent. Said pharmaceutical compositions can be applied e.g. orally, topically, intravenously, intraperitoneally, subcutaneously and rectally in pharmaceutically effective amounts.

In the following Examples, the anti-tumor active substances are tested by in vitro tests using intact tumor cells. Furthermore, a comparison of the activity test results and the tests evaluating the ability to penetrate cellular membranes shows that indigoid bisindole compounds which exhibit a good cell-penetrating ability show good to excellent anti-tumor activity.

The present invention is explained in detail by the following examples by which also further advantages of the present invention will become apparent.

EXAMPLES

1. Synthesis of the Compounds

The following general procedures were used to synthesize the indirubin derivatives according to Examples 1 to 69.

Synthesis of Indirubines

Method I

According to this method Examples 1–14 and 22–24 were prepared.

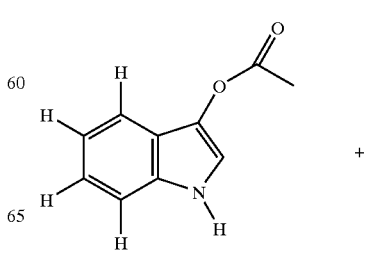

+

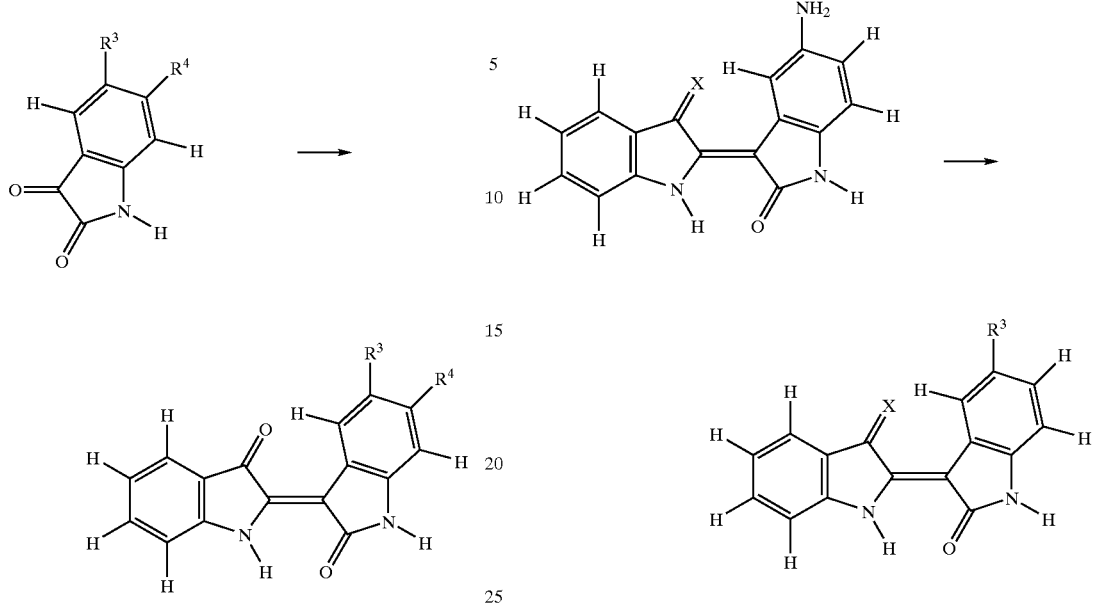

The indirubin derivatives are prepared according to Russel G. A., Kaupp G. (1969), J. Am. Chem. Soc., 91, pages 3851–3859.

Method II

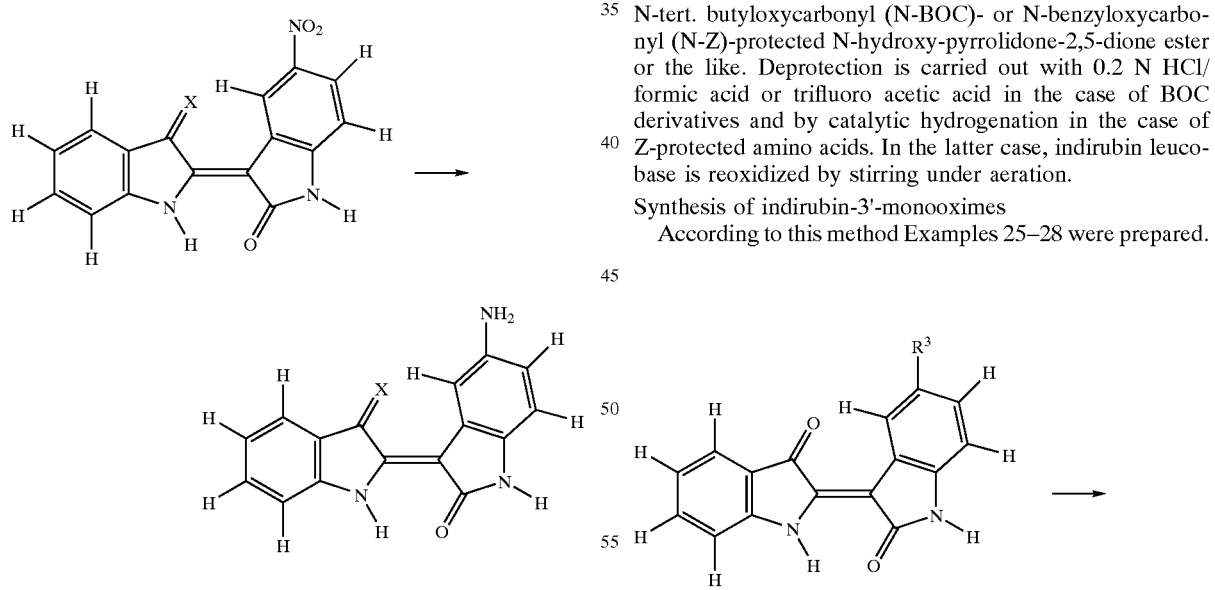

Example 15 is prepared by reducing 5-nitro-indirubin with iron/0.2 N HCl in ethanol at 80° C. The filtrate is neutralized by NaOH and stirred under aeration to reoxidize the leucobase to 5-amino-indirubin.

Method III

According to this method Examples 16–21 and 29–30 were prepared.

5-amino-indirubin or 5-amino-indirubin-3′-monooxime are suspended under stirring in pyridine containing catalytic amounts of a suitable base like N,N-dimethylaminopyridine, N-methylmorpholine or N,N,N,N-tetramethyl-guanidine. Using general methods of peptide chemistry, 5-amino-indirubin or 5-amino-indirubin-3′-monooxime is acylated with suitably activated acids, such as acyl chloride, acyl anhydrides or N-protected amino acid active esters, such as N-tert. butyloxycarbonyl (N-BOC)- or N-benzyloxycarbonyl (N-Z)-protected N-hydroxy-pyrrolidone-2,5-dione ester or the like. Deprotection is carried out with 0.2 N HCl/ formic acid or trifluoro acetic acid in the case of BOC derivatives and by catalytic hydrogenation in the case of Z-protected amino acids. In the latter case, indirubin leucobase is reoxidized by stirring under aeration.

Synthesis of indirubin-3′-monooximes

According to this method Examples 25–28 were prepared.

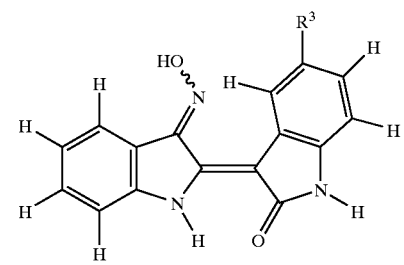

The indirubin-3'-monooxime derivatives were prepared as described in Farbwerke vorm. Meister Lucius & Brüning in Hoechst a. M. (1913), DRP 283726.

Method I

According to this method Examples 31–49, 53, 54, 67 and 68 were prepared.

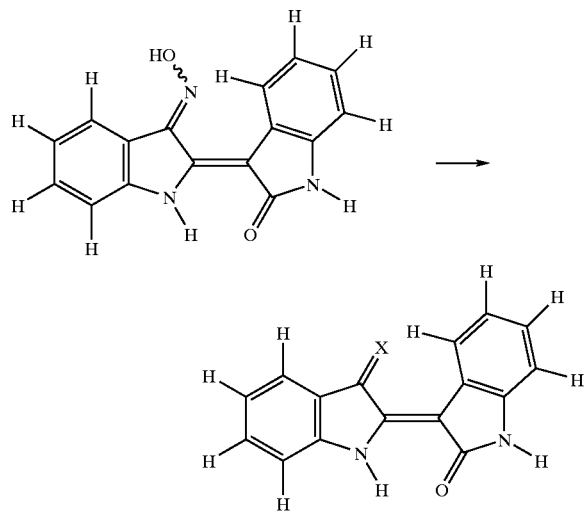

To a mixture of indirubin-3'-monooxime with 1–8 equivalents of a halogene alkane (Halogenes are Cl, Br or J) in a suitable solvent, such as tetrahydrofurane, dioxane, diglyme, methanol, ethanol, propanol or butanol, a suitable base is added (1–10 equivalents). The base is preferably N,N,N,N-tetramethyl-guanidine or other inorganic (KOH, NaOH) or organic bases (pyridine, triethylamine and the like). The reaction mixture is stirred for 0.5 to 10 h at room temperature or elevated temperature (up to 100° C.), depending on the solvent used. After termination of the reaction, the product precipitates and is filtered off.

Method II

According to this method Examples 50–52 were prepared.

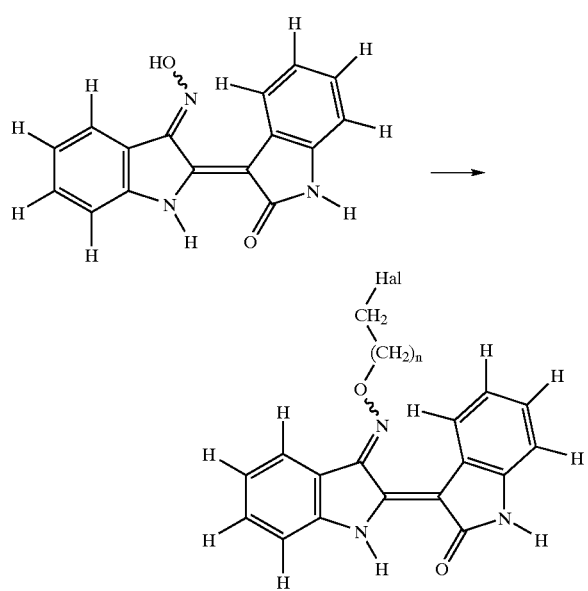

A solution of indirubin-3'-monooxime, N,N,N,N-tetramethyl-guanidine (1–4 equivalents) and ethanol is added dropwise to a solution of a suitable dihalogene alkane in ethanol. The dihalogene alkane preferably is 1,2- to 1,18-dibromo alkane or dichloro alkane. The precipitated product is filtered off and washed with ethanol.

Method III

According to this method Examples 55–66 and 69 were prepared.

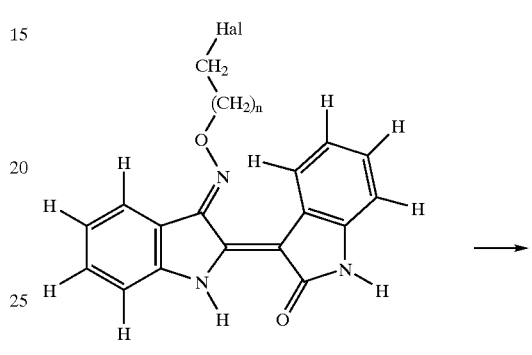

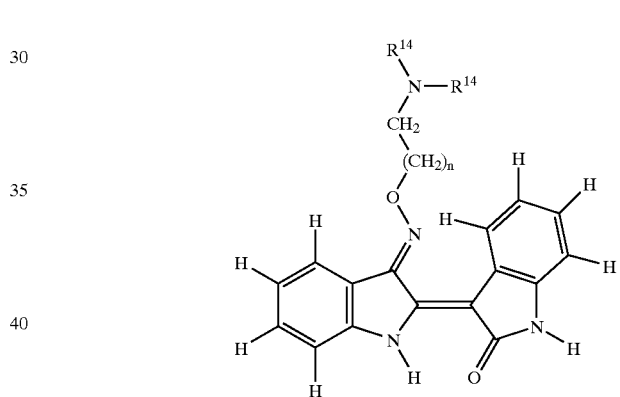

The indirubin-3'-monooxime-halogene-alkyl-ether is dissolved in dimethylsulfoxide or ethanol or a mixture of both. The appropiate amine is added stepwise and the reaction mixture stirred for 5–24 h at room temperature or elevated temperature (up to 150° C.), depending on the solvent and the amino compound.

Method IV

Example 53 and 54 were prepared as described by Method I. The N-acylated aminoglycoside was deprotected using general methods of carbohydrate chemistry. Removal of the N-acyl group was carried out using acetyl bromide as described by Micheel, Lengsfeld, Chem. Ber., 89, 1246–1250, 1956. O-acetyl groups were removed with sodium ethanolate.

Synthesis of the Halogenealkane-o-glycoside-ethers

The halogenealkane-o-glycoside-ethers are prepared according to common methods of carbohydrate chemistry.

Method I
According to this method Examples A–F were prepared.

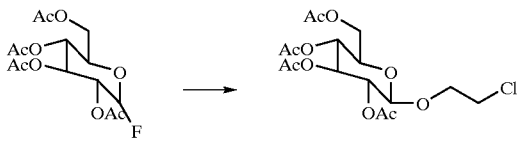

In accordance to R. Miethchen and V. Fehring, Liebigs Ann./Recueil, 553–561, 1997.

A solution of 2,3,4,6-tetra-O-acetyl-α-D-glucopyranosylfluoride (3.26 mmol) and 2-chloroethanol (3.35 mmol) in acetonitrile is mixed with 0.5 ml $F_3B*Et_2O$ and stirring is continued for 30 min. After addition of dichloromethane (60 ml), the mixture is filtered trough silica gel. The filtrate is washed with aqueous $NaHCO_3$ and water. The dried organic phase is evaporated under reduced pressure and the compound recrystallized from hexane.

Method II
According to this method Example G was prepared.

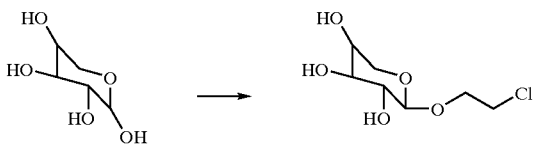

This synthesis follows a procedure described by L. Hough, K. C. McCarthy, A. C. Richardson, Recl. Trav. Chim. Pays-Bas, 110, 450–458, 1991. A mixture of L-arabinose (33 mmol), 2-chloroethanol (20 ml) and acetyl chloride (0.5 ml) was stirred at 60° C. for 24 h. The mixture was allowed to cool to room temperature and the crystalline precipitate filtered off and washed with acetone.

Identity and homogeneity of the compounds were established by elemental analysis and thin layer chromatography. Where necessary, structural confirmation was obtained by NMR ($^1H$ and $^{13}C$).

Example A 2-chloroethyl-2,3,4,6-tetraacetyl-D-glucopyranoside

Yield: 79%, fine needles
CHN-analysis: $C_{16}H_{23}O_{10}Cl$ (MW: 410.81 g/mol) calc.: 46.7%; C, 5.64%; H. found: 46.8%; C, 5.7%; H.

Example B 2-chloroethyl-2,3,4,6-tetraacetyl-D-galactopyranoside

Yield: 76%, fine needles
CHN-analysis: $C_{16}H_{23}O_{10}Cl$ (MW: 410.81 g/mol) calc.: 46.7%; C, 5.6%; H. found: 46.8%; C, 5.7%; H.

Example C 3-chloropropyl-2,3,4,6-tetraacetyl-D-glucopyranoside

Yield: 74%, amorphous solid
CHN-analysis: $C_{17}H_{25}O_{10}Cl$ (MW: 424.83 g/mol) calc.: 48.0%; C, 5.9%; H. found: 48.1%; C, 5.9%; H.

Example D 2-chloroethyl-2,3,6,8,9,10,12-heptaacetyl-$O^4$-a-D-glucopyranosyl-D-glucopyranoside Yield: 76%, amorphous solid
CHN-analysis: $C_{28}H_{39}O_{18}Cl$ (MW: 699.06 g/mol) calc.: 48.1%; C, 5.6%; H. found: 48.2%; C, 5.7%; H.

Example E 2-chloroethyl-N,3,4,6-tetraacetyl-2-deoxy-amino-D-glucopyranoside

Yield: 74%, fine needles
CHN-analysis: $C_{16}H_{24}O_9NCl$ (MW: 409.82 g/mol) calc.: 46.9%; C, 5.9%; H, 3.42%; N. found: 46.9%; C, 5.9%; H, 3.51%; N.

Example F 2-chloroethyl-N,3,4,6-tetraacetyl-2-deoxy-amino-D-galactopyranoside

Yield: 72%, fine needles
CHN-analysis: $C_{16}H_{24}O_9NCl$ (MW: 409.82 g/mol) calc.: 46.9%; C, 5.9%; H, 3.4%; N. found: 47.0%; C, 6.1%; H, 3.5%; N.

Example G 2-chloroethyl-L-arabinose

Yield: 24%, fine needles
CHN-analysis: $C_7H_{13}O_5Cl$ (MW: 212.63 g/mol) calc.: 39.5%; C, 6.2%; H. found: 39.6%; C, 6.4%; H.

Example 1

6-iodo-indirubin

Yield: 68%, fine deep-purple powder
CHN-analysis: $C_{16}H_9IN_2O_2$ (MW: 388.16 g/mol) calc.: 49.5%; C, 2.3%; H, 7.2%; N. found: 49.3%; C, 2.1%; H, 7.1%; N.

Example 2

5-ethyl-indirubin

Yield: 92%, fine deep-purple powder
CHN-analysis: $C_{18}H_{14}N_2O_2$ (MW: 290.32 g/mol) calc.: 74.5%; C, 4.9%; H, 9.7%; N. found: 74.2%; C, 4.8%; H, 9.5%; N.

Example 3

5-isopropyl-indirubin

Yield: 94%, fine deep-purple powder
CHN-analysis: $C_{19}H_{19}N_2O_2$ (MW: 304.35 g/mol) calc.: 75.0%; C, 5.3%; H, 9.2%; N. found: 74.8%; C, 5.2%; H, 9.1%; N.

Example 4

5-n-propyl-indirubin

Yield: 93%, fine deep-purple powder
CHN-analysis: $C_{19}H_{16}N_2O_2$ (MW: 304.35 g/mol) calc.: 75.0%; C, 5.3%; H, 9.2%; N. found: 74.9%; C, 5.3%; H, 9.1%; N.

Example 5

5-(carboxymethyl)-indirubin

Yield: 66%, fine deep-purple crystals
CHN-analysis: $C_{19}H_{16}N_2O_4$ (MW: 320.30 g/mol) calc.: 67.5%; C, 3.8%; H, 8.8%; N. found: 67.2%; C, 3.6%; H, 8.8%; N.

Example 6

5-[2-(piperazin-1-yl)-ethan-2-one-1-yl]-indirubin

Yield: 55%, fine deep-purple crystals
CHN-analysis: $C_{22}H_{21}N_4O_3$ (MW: 389.43 g/mol) calc.: 67.9%; C, 5.4%; H, 14.4%; N. found: 68.1%; C, 5.7%; H, 14.6%; N.

Example 7

5-[2-(morpholin-4-yl)-ethan-2-one-1-yl]-indirubin

Yield: 53%, fine deep-purple crystals
CHN-analysis: $C_{22}H_{20}N_3O_4$ (MW: 390.42 g/mol) calc.: 67.7%; C, 5.2%; H, 10.8%; N. found: 67.8%; C, 5.3%; H, 11.0%; N.

Example 8

N-(2-amino-ethyl)-2-[3-(3'-oxo-(2'H3'H)indol-2'-ylidene)-(2H3H)indol-2-one-5-yl]-acetamide Yield: 63%, fine deep-purple crystals
CHN-analysis: $C_{20}H_{18}N_4O_3$ (MW: 362.39 g/mol) calc.: 66.3%; C, 5.0%; H, 15.5%; N. found: 66.5%; C, 5.1%; H, 15.6%; N.

Example 9

N-methyl-2-[3-(3'-oxo-(2'H3'H)indol-2'-ylidene)-(2H3H)indol-2-one-5-yl]-acetamide Yield: 61%, fine deep-purple crystals
CHN-analysis: $C_{19}H_{15}N_3O_3$ (MW: 333.35 g/mol) calc.: 68.5%; C, 4.5%; H, 12.6%; N. found: 68.4%; C, 4.5%; H, 12.5%; N.

Example 10

N,N-dimethyl-2-[3-(3'-oxo-(2'H3'H)indol-2'-ylidene)-(2H3H)indol-2-one-5-yl]-acetamide Yield: 59%, fine deep-purple crystals
CHN-analysis: $C_{20}H_{17}N_3O_3$ (MW: 347.37 g/mol) calc.: 69.2%; C, 4.5%; H, 12.1%; N. found: 69.1%; C, 4.5%; H, 12.2%; N.

Example 11

2-{2-[3-(3'-oxo-(2'H3'H)indol-2'-ylidene)-(2H3H)indol-2-one-5-yl]-acetylamino}-acetic Acid Yield: 55%, fine deep-purple crystals
CHN-analysis: $C_{20}H_{15}N_3O_5$ (MW: 377.35 g/mol) calc.: 63.7%; C, 4.0%; H, 11.1%; N. found: 63.7%; C, 4.1%; H, 11.0%; N.

Example 12 methyl-2-{2-[3-(3'-oxo-(2'H3'H)indol-2'-ylidene)-(2H3H)indol-2-one-5-yl]-acetylamino}-acetate Yield: 57%, fine deep-purple crystals
CHN-analysis: $C_{21}H_{17}N_3O_5$ (MW: 391.38 g/mol) calc.: 64.5%; C, 4.4%; H, 10.7%; N. found: 64.4%; C, 4.5%; H, 10.8%; N.

Example 13

[3-(3'-oxo-(2'H3'H)indol-2'-ylidene)-(2H3H)indol-2-one-5-yl]-methyl-phosphonic Acid Yield: 61%, fine deep-purple crystals
CHN-analysis: $C_{17}H_{13}N_2O_5P$ (MW: 356.28 g/mol) calc.: 57.3%; C, 3.7%; H, 7.9%; N. found: 57.2%; C, 3.6%; H, 7.9%; N.

Example 14 diethyl-{[3-(3'-oxo-(2'H3'H)indol-2'-ylidene)-(2H3H)indol-2-one-5-yl]-methyl}-phosphonate Yield: 57%, fine deep-purple crystals
CHN-analysis: $C_{21}H_{21}N_2O_5P$ (MW: 412.38 g/mol) calc.: 61.2%; C, 5.1%; H, 6.8%; N. found: 61.2%; C, 5.2%; H, 6.9%; N.

Example 15

5-amino-indirubin

Yield: 72%, fine deep-purple crystals
CHN-analysis: $C_{16}H_{11}N_3O_2$ (MW: 277.28 g/mol) calc.: 69.3%; C, 4.0%; H, 15.2%; N. found: 69.2%; C, 3.9%; H, 15.4%; N.

Example 16

5-acetylamino-indirubin

Yield: 64%, fine deep-purple crystals
CHN-analysis: $C_{18}H_{13}N_3O_3$ (MW: 319.32 g/mol) calc.: 67.7%; C, 4.1%; H, 13.2%; N. found: 67.6%; C, 4.2%; H, 13.3%; N.

Example 17

[3-(3'-oxo-(2'H3'H)indol-2'-ylidene)-(2H3H)indol-2-one-5-yl]-succinamic acid

Yield: 48%, fine deep-purple crystals
CHN-analysis: $C_{20}H_{15}N_3O_5$ (MW: 377.35 g/mol) calc.: 63.7%; C, 4.0%; H, 11.1%; N. found: 63.6%; C, 4.1%; H, 11.1%; N.

Example 18

2-amino-N-[3-(3'-oxo-(2'H3'H)indol-2'-ylidene)-(2H3H)indol-2-one-5-yl]-acetamide Yield: 60%, fine deep-purple crystals
CHN-analysis: $C_{18}H_{14}N_4O_3$ (MW: 334.33 g/mol) calc.: 64.7%; C, 4.2%; H, 16.8%; N. found: 64.6%; C, 4.2%; H, 16.7%; N.

Example 19

2-amino-N-[3-(3'-oxo-(2'H3'H)indol-2'-ylidene)-(2H3H)indol-2-one-5-yl]-propionamide Yield: 64%, fine deep-purple crystals
CHN-analysis: $C_{19}H_{16}N_4O_3$ (MW: 348.36 g/mol) calc.: 65.5%; C, 4.6%; H, 16.1%; N. found: 65.6%; C, 4.4%; H, 16.0%; N.

Example 20

5-(2-amino-ethyl)-amino-indirubin

Yield: 52%, fine deep-purple crystals
CHN-analysis: $C_{18}H_{16}N_4O_2$ (MW: 348.36 g/mol) calc.: 67.5%; C, 5.0%; H, 17.5%; N. found: 67.6%; C, 5.1%; H, 17.3%; N.

Example 21

5-(2-hydroxy-ethyl)-amino-indirubin

Yield: 55%, fine deep-purple crystals
CHN-analysis: $C_{18}H_{15}N_3O_3$ (MW: 321,33 g/mol) calc.: 67.3%; C, 4.7%; H, 13.1%; N. found: 67.5%; C, 4.8%; H, 13.0%; N.

Example 22 indirubin-5-sulfonic acid-(piperazin-1-yl-amide)

Yield: 42%, fine deep-purple crystals
CHN-analysis: $C_{20}H_{18}N_4O_4S$ (MW: 410.45 g/mol) calc.: 58.5%; C, 4.4%; H, 13.7%; N. found: 58.6%; C, 4.6%; H, 13.8%; N.

Example 23 indirubin-5-sulfonic acid-(morpholin-4-yl-amide)

Yield: 42%, fine deep-purple crystals
CHN-analysis: $C_{20}H_{17}N_3O_5S$ (MW: 411.43 g/mol) calc.: 58.4%; C, 4.2%; H, 10.2%; N. found: 58.5%; C, 4.4%; H, 10.3%; N.

Example 24 methyl-2-{[3-(3'-oxo-(2'H3'H)indol-2'-ylidene)-(2H3H)indol-2-one-5-yl]-sulfonylamino}-acetate Yield: 39%, fine deep-purple crystals
CHN-analysis: $C_{19}H_{15}N_3O_6S$ (MW: 413.41 g/mol) calc.- 55.2%; C, 3.7%; H, 10.2%; N. found: 55.4%; C, 3.7%; H, 10.3%; N.

Example 25

5-methyl-indirubin-3'-monooxime

Yield: 56%, red crystals
CHN-analysis: $C_{17}H_{13}N_3O_2$ (MW: 291.31 g/mol) calc.: 70.1%; C, 4.5%; H, 14.4%; N. found: 69.9%; C, 4.5%; H, 14.3%; N.

Example 26

5-ethyl-indirubin-3'-monooxime

Yield: 91%, red crystals
CHN-analysis: $C_{18}H_{15}N_3O_2$ (MW: 305.34 g/mol) calc.: 70.8%; C, 5.0%; H, 13.8%; N. found: 70.6%; C, 4.9%; H, 13.8%; N.

Example 27

5-isopropyl-indirubin-3'-monooxime

Yield: 42%, red crystals
CHN-analysis: $C_{19}H_{17}N_3O_2$ (MW: 319.36 g/mol) calc.: 71.5%; C, 5.4%; H, 13.2%; N. found: 71.2%; C, 5.2%; H, 13.1%; N.

Example 28

5-amino-indirubin-3'-monooxime

Yield: 58%, red crystals
CHN-analysis: $C_{16}H_{12}N_4O_2$ (MW: 292.30 g/mol) calc.: 65.8%; C, 4.1%; H, 19.2%; N. found: 65.7%; C, 4.1%; H, 19.1%; N.

Example 29

5-acetylamino-indirubin-3'-monooxime

Yield: 52%, red crystals
CHN-analysis: $C_{18}H_{14}N_4O_3$ (MW: 334.33 g/mol) calc.: 64.7%; C, 4.2%; H, 16.8%; N. found: 64.7%; C, 4.1%; H, 16.9%; N.

Example 30

2-amino-N-[3-(3'-hydroxyimino-(2H3H)indol-2'-ylidene)-(2H3H)-indol-2-one-5-yl]-acetamide Yield: 62%, red crystals
CHN-analysis: $C_{18}H_{15}N_5O_3$ (MW: 349.35 g/mol) calc.: 61.9%; C, 4.3%; H, 20.1%; N. found: 62.0%; C, 4.1%; H, 19.9%; N.

Example 31

3-[3'-(iminooxy-O-(2-hydroxy-ethyl)-(2'H3'H)indol-2'-ylidene]-(2H3H)indol-2-one

Yield: 79%, red powder
CHN-analysis: $C_{18}H_{15}N_3O_3$ (MW: 321.33 g/mol) calc.: 67.3%; C, 4.7%; H, 13.1%; N. found: 67.2%; C, 4.8%; H, 13.0%; N.

Example 32

3-[3'-(iminooxy-O-(3-hydroxy-propyl)-(2'H3'H)indol-2'-ylidene]-(2H3H)indol-2-one Yield: 83%, red powder
CHN-analysis: $C_{19}H_{17}N_3O_3$ (MW: 335.36 g/mol) calc.: 68.1%; C, 5.1%; H, 12.5%; N. found: 67.9%; C, 5.2%; H, 12.4%; N.

Example 33

3-{3'-[iminooxy-O-(2-(2-hydroxy-ethoxy)-ethyl)]-(2'H3'H)indol-2'-ylidene}-(2H3H)indol-2-one Yield: 64%, red powder
CHN-analysis: $C_{20}H_{19}N_3O_4$ (MW: 365.39 g/mol) calc.: 65.8%; C, 5.2%; H, 11.5%; N. found: 65.6%; C, 5.2%; H, 11.4%; N.

Example 34

3-{3'-[iminooxy-O-((2-hydroxy-2-methyl)-propyl)]-(2'H3'H)indol-2'-ylidene}-(2H3H)indol-2-one Yield: 90%, red powder
CHN-analysis: $C_{20}H_{19}N_3O_3$ (MW: 349.39 g/mol) calc.: 68.8%; C, 5.5%; H, 12.0%; N. found: 68.7%; C, 5.5%; H, 12.0%; N.

Example 35

2-{O-[2'-(2-oxo-(2H3H)indol-3-ylidene)-(2'H3'H)indol-3'-ylidene]-aminooxy}-acetic Acid (Sodium Salt)

Yield: 57%, red powder
CHN-analysis: $C_{18}H_{12}N_3O_4Na$ (MW: 357.30 g/mol) calc.: 60.5%; C, 3.4%; H, 11.8%; N. found: 60.3%; C, 3.6%; H, 11.7%; N.

Example 36

3-{O-[2'-(2-oxo-(2H3H)indol-3-ylidene)-(2'H3'H)indol-3'-ylidene]-aminooxy}-propionic Acid (Sodium Salt)

Yield: 59%, red powder
CHN-analysis: $C_{19}H_{14}N_3O_4Na$ (MW: 371.33 g/mol) calc.: 61.5%; C, 3.8%; H, 11.3%; N. found: 61.4%; C, 3.6%; H, 11.4%; N.

Example 37

4-{O-[2'-(2-oxo-(2H3H)indol-3-ylidene)-(2'H3'H)indol-3'-ylidene]-aminooxy}-butyric Acid (Sodium Salt)

Yield: 58%, red powder
CHN-analysis: $C_{20}H_{16}N_3O_4Na$ (MW: 385.35 g/mol) calc.: 62.3%; C, 4.2%; H, 10.9%; N. found: 62.0%; C, 4.3%; H, 11.0%; N.

Example 38

5{O-[2'-(2-oxo-(2H3H)indol-3-ylidene)-(2'H3'H)indol-3'-ylidene]-aminooxy}-pentanoic Acid (Sodium Salt)

Yield: 52%, red powder
CHN-analysis: $C_{21}H_{18}N_3O_4Na$ (MW: 399.38 g/mol) calc.: 63.2%; C, 4.5%; H, 10.5%; N. found: 63.0%; C, 4.4%; H, 10.7%; N.

Example 39

3-[3'-(iminooxy-O-carbethoxy)-(2'H3'H)indol-2'-ylidene]-(2H3H)indol-2-one

Yield: 82%, red powder
CHN-analysis: $C_{19}H_{15}N_3O_4$ (MW: 349.34 g/mol) calc.: 65.3%; C, 4.3%; H, 12.0%; N. found: 65.3%; C, 4.4%; H, 11.9%; N.

Example 40 ethyl-2{O-[2'-(2-oxo-(2H3H)indol-3-ylidene)-(2'H3'H)indol-3'-ylidene]-aminooxy}-acetate Yield: 31%, red powder
CHN-analysis: $C_{20}H_{17}N_3O_4$ (MW: 363.37 g/mol) calc.: 66.1%; C, 4.7%; H, 11.6%; N. found: 66.2%; C, 4.6%; H, 11.5%; N.

Example 41

3-{3'-[iminooxy-O-((N,N)-dimethyl-carbamoyl)]-(2'H3'H)indol-2'-ylidene}-(2H3H)indol-2-one Yield: 89%, red powder
CHN-analysis: $C_{19}H_{18}N_4O_3$ (MW: 348.36 g/mol) calc.: 65.5%; C, 4.6%; H, 16.1%; N. found: 65.2%; C, 4.5%; H, 15.9%; N.

Example 42

2-{O-[2'-(2-oxo-(2H3H)indol-3-ylidene)-(2'H3'H)indol-3'-ylidene]-aminooxy}-acetamide Yield: 86%, red powder
CHN-analysis: $C_{18}H_{14}N_4O_3$ (MW: 334.33 g/mol) calc.: 64.7%; C, 4.2%; H, 16.8%; N. found: 64.8%; C, 4.4%; H, 16.5%; N.

Example 43

N,N-dimethyl-2{O-[2'-(2-oxo-(2H3H)indol-3-ylidene)-(2'H3'H)indol-3'-ylidene]-aminooxy}-acetamide Yield: 89%, red powder
CHN-analysis: $C_{18}H_{14}N_4O_3$ (MW: 362.39 g/mol) calc.: 66.3%; C, 5.0%; H, 15.5%; N. found: 66.1%; C, 4.7%; H, 15.5%; N.

Example 44

2-{2-[O-(2'-(2-oxo-(2H3H)indol-3-ylidene)-(2'H3'H)indol-3'-ylidene)-aminooxy]-acetylamino}-acetic Acid Yield: 79%, red powder CHN-analysis: $C_{20}H_{16}N_4O_5$ (MW: 392.37 g/mol) calc. 61.2%; C, 4.1%; H, 14.3%; N. found: 61.3%; C, 4.0%; H, 14.1%; N.

Example 45

3-{3'-[iminooxy-O-(3-D-glucopyranosylpropyl)]-(2'H3'H)indol-2'-ylidene}-(2H3H)indol-2-one Yield: 28%, red powder CHN-analysis: $C_{25}H_{25}N_3O_8$ (MW: 495.49 g/mol) calc.: 60.6%; C. 5.1%; H. 8.5%; N. found: 60.8%; C. 5.2%; H. 8.6%; N.

Example 46

3-{3'-[iminooxy-O-($O^4$-α-D-glucopyranosyl-2-D-glucopyranosylethyl)]-(2'H3'H)indol-2'-ylidene}-(2H3H)indol-2-one Yield: 20%, red powder CHN-analysis: $C_{31}H_{34}N_3O_{13}$ (MW: 656.62 g/mol) calc.: 56.7%; C. 5.2%; H. 6.4%; N. found: 56.9%; C. 5.3%; H. 6.5%; N.

Example 47

3-{3'-[iminooxy-O-(2-D-galactopyranosylethyl)]-(2'H3'H)indol-2'-ylidene}-(2H3H)indol-2-one Yield: 32%, red powder CHN-analysis: $C_{24}H_{25}N_3O_8$ (MW: 483.48 g/mol) calc.: 56.5%; C. 5.5%; H. 8.2%; N. found: 56.7%; C. 5.3%; H. 8.3%; N.

Example 48

3-{3'-[iminooxy-O-(2-D-glucopyranosylethyl)]-(2'H3'H)indol-2'-ylidene}-(2H3H)indol-2-one Yield: 41%, red powder CHN-analysis: $C_{24}H_{25}N_3O_8$ (MW: 483.48 g/mol) calc.: 56.5%; C. 5.5%; H. 8.2%; N. found: 56.7%; C. 5.4%; H. 8.3%; N.

Example 49

3-{3'-[iminooxy-O-(2-L-arabinopyranosylethyl)]-(2'H3'H)indol-2'-ylidene}-(2H3H)indol-2-one Yield: 43%, red powder CHN-analysis: $C_{23}H_{22}N_3O_7$ (MW: 452.44 g/mol) calc.: 61.1%; C. 4.9%; H. 9.3%; N. found: 61.2%; C. 5.0%; H. 9.4%; N.

Example 50

3-{3'-[iminooxy-O-(2-chloroethyl)]-(2'H3'H)indol-2'-ylidene}-(2H3H)indol-2-one

Yield: 97%, red needles

CHN-analysis: $C_{18}H_{14}N_3O_2Cl$ (MW: 339.78 g/mol) calc.: 63.6%; C. 4.2%; H. 12.4%; N. found: 63.8%; C. 4.4%; H. 12.5%; N.

Example 51

3-{3'-[iminooxy-O-(4-chlorobutyl)](2'H3'H)indol-2'-ylidene}-(2H3H)indol-2-one

Yield: 96%, red needles

CHN-analysis: $C_{20}H_{18}N_3O_2Cl$ (MW: 367.83 g/mol) calc.: 65.3%; C. 4.9%; H. 11.4%; N. found: 65.5%; C. 4.8%; H. 12.5%; N.

Example 52

3-{3'-[iminooxy-O-(10-chlorodecyl)]-(2'H3'H)indol-2'-ylidene}-(2H3H)indol-2-one

Yield: 95%, red needles

CHN-analysis: $C_{26}H_{30}N_3O_2Cl$ (MW: 452.00 g/mol) calc.: 69.1%; C. 6.7%; H. 9.3%; N. found: 69.3%; C. 6.8%; H. 9.4%; N.

Example 53

3-{3'-[iminooxy-O-(2-(2-amino-2-deoxy-D-glucopyranosyl)-ethyl)]-(2'H3'H)indol-2'-ylidene}-(2H3H)indol-2-one Yield: 29%, red powder CHN-analysis: $C_{24}H_{26}N_4O_7$ (MW: 482.49 g/mol) calc.: 59.7%; C. 5.4%; H. 11.6%; N. found: 59.9%; C. 5.4%; H. 11,7%; N.

Example 54

3-{3'-[iminooxy-O-(2-(2-amino-2-deoxy-D-galactopyranosyl)-ethyl)]-(2'H3'H)indol-2'-ylidene}-(2H3H)indol-2-one Yield: 26%, red powder CHN-analysis: $C_{24}H_{26}N_4O_7$ (MW: 482.49 g/mol) calc.: 59.7%; C. 5.4%; H. 11.6%; N. found: 59.9%; C. 5.6%; H. 11,7%; N.

Example 55

3-{3'-[iminooxy-O-(N-(1-deoxy-glucitol)-2-aminoethyl)]-(2'H3'H)indol-2'-ylidene}-(2H3H)indol-2-one Yield: 43%, red powder CHN-analysis: $C_{24}H_{28}N_4O_7$ (MW: 484.51 g/mol) calc.: 59.5%; C. 5.8%; H. 11.6%; N. found: 59.6%; C. 6.0%; H. 11.7%; N.

Example 56

3-{3'-[iminooxy-O-(N-(2-deoxy-glucose)-2-amino-ethyl)] -(2'H3'H)indol-2'-ylidene}-(2H3H)indol-2-one Yield: 48%, red powder
CHN-analysis: $C_{24}H_{26}N_4O_7$ (MW: 482.49 g/mol) calc.: 59.7%; C. 5.4%; H. 11.6%; N. found: 59.9%; C. 5.5%; H. 11,8%; N.

Example 57

3-{3'-[iminooxy-O-(N-(2-deoxy-galactose)-2-amino-ethyl)] -(2'H3'H)indol-2'-ylidene}-(2H3H)indol-2-one Yield: 46%, red powder
CHN-analysis: $C_{24}H_{26}N_4O_7$ (MW: 482.49 g/mol) calc.: 59.7%; C. 5.4%; H. 11.6%; N. found: 59.8%; C. 5.4%; H. 11,7%; N.

Example 58

3-{3'-[iminooxy-O-((N,N)-dimethyl-2-amino-ethyl)]-(2'H3'H)indol-2'-ylidene}-(2H3H)indol-2-one Yield: 48%, red powder
CHN-analysis: $C_{20}H_{20}N_4O_2$ (MW: 348.40 g/mol) calc.: 69.0%; C. 6.8%; H. 16.1%; N. found: 69.2%; C. 6.9%; H. 16.2%; N.

Example 59

3-{3'-[iminooxy-O-(N-hydroxyethyl-2-amino-ethyl)]-(2'H3'H)indol-2'-ylidene}-(2H3H)indol-2-one Yield: 47%, red powder
CHN-analysis: $C_{20}H_{20}N_4O_3$ (MW: 364.40 g/mol) calc.: 65.9%; C. 5.5%; H. 15.4%; N. found: 66.1%; C. 5.6%; H. 15.5%; N.

Example 60

3-{3'-[iminooxy-O-((N,N)-bis(hydroxyethyl)-2-amino-ethyl)] -(2'H3'H)indol-2'-ylidene}-(2H3H)indol-2-one Yield: 47%, red powder
CHN-analysis: $C_{22}H_{24}N_4O_4$ (MW: 408.46 g/mol) calc.: 64.7%; C. 5.9%; H. 13.7%; N. found: 64.9%; C. 6.1%; H. 13.8%; N.

Example 61

3-{3'-[iminooxy-O-((N,N)-bis(hydroxyethyl)-4-amino-butyl)] -(2H3H)indol-2'-ylidene}-(2H3H)indol-2-one Yield: 46%, red powder
CHN-analysis: $C_{26}H_{32}N_4O_7$ (MW: 512.56 g/mol) calc.: 60.9%; C. 6.3%; H. 10.9%; N. found: 61.1%; C. 6.4%; H. 11.0%; N.

Example 62

3-{3'-[iminooxy-O-((N,N-bis(hydroxyethyl)-10-amino-decyl)] -(2'H3'H)indol-2'-ylidene}-(2H3H)indol-2-one Yield: 48%, red powder
CHN-analysis: $C_{32}H_{44}N_4O_7$ (MW: 596.72 g/mol) calc.: 64.4%; C. 7.4%; H. 9.4%; N. found: 64.5%; C. 7.5%; H. 9.4%; N.

Example 63

3-{3'-[iminooxy-O-(2-(piperazin-1-yl)-ethyl)]-(2'H3'H)indol-2'-ylidene}-(2H3H)indol-2-one Yield: 47%, red powder
CHN-analysis: $C_{22}H_{23}N_5O_2$ (MW: 389.46 g/mol) calc.: 67.8%; C. 5.9%; H. 18.0%; N. found: 67.9%; C. 6.1%; H. 18.1%; N.

Example 64

3-{3'-[iminooxy-O-(2-(morpholin-4-yl)-ethyl)]-(2'H3')indol-2'-ylidene}-(2H3H)indol-2-one Yield: 48%, red powder
CHN-analysis: $C_{22}H_{23}N_4O_3$ (MW: 391.45 g/mol) calc.: 67.5%; C. 5.9%; H. 14.3%; N. found: 67.6%; C. 6.1%; H. 14.5%; N.

Example 65

3-{3'-[iminooxy-O-(2-(4-methyl-piperazin-1-yl)-ethyl)]-(2'H3'H)indol-2'-ylidene}-(2H3H)indol-2-one Yield: 47%, red powder
CHN-analysis: $C_{23}H_{25}N_5O_2$ (MW: 403.48 g/mol) calc.: 68.5%; C. 6.3%; H. 17.4%; N. found: 68.7%; C. 6.2%; H. 17.3%; N.

Example 66

3-{3'-[iminooxy-O-(2-(2-amino-ethyl)-amino-ethyl)]-(2'H3'H)indol-2'-ylidene}-(2H3H)indol-2-one Yield: 46%, red needles
CHN-analysis: $C_{20}H_{21}N_2O_2$ (MW: 321.40 g/mol) calc.: 74.7%; C. 6.6%; H. 8.7%; N. found: 74.9%; C. 6.8%; H. 8.8%; N.

Example 67

3-[3'-[iminooxy-O-(2-hydroxy-ethyl)]-(2H'3H')indol-2'-ylidene]-5-methyl-(2H3H)indol-2-one Yield: 77%, red powder
CHN-analysis: $C_{19}H_{17}N_3O_3$ (MW: 335.36 g/mol) calc.: 68.1%; C, 5.1%; H, 12.5%; N. found: 68.2%; C, 5.2%; H, 12.6%; N.

Example 68

3-[3'-[iminooxy-O-(2-D-glucopyranosylethyl)]-(2H'3H')indol-2'-ylidene]-5-methyl-(2H3H)indol-2-one Yield: 44%, red powder
CHN-analysis: $C_{25}H_{27}N_3O_8$ (MW: 497.50 g/mol) calc.: 60.4%; C. 5.5%; H. 8.5%; N. found: 60.6%; C. 5.6%; H. 8.7%; N.

Example 69

3-[3'-[iminooxy-O-(N-(1-deoxy-glucitol)-2-amino-ethyl)] -(2H'3H')indol-2'-ylidene]-5-methyl-(2H3H)indol-2-one Yield: 43%, red powder
CHN-analysis: $C_{25}H_3N_4O_7$ (MW: 498.54 g/mol) calc.: 60.2%; C. 6.1%; H. 11.2%; N. found: 60.4%; C. 6.2%; H. 11.4%; N.

Table 1 summarizes the structures of the indirubin compounds of Examples 1 to 30.

TABLE 1

| Example | $R^3$ | $R^4$ | X |
|---|---|---|---|
| 1 | H | I | O |
| 2 | $CH_2$—$CH_3$ | H | O |
| 3 | $CH(CH_3)_2$ | H | O |
| 4 | $CH_2$—$CH_2$—$CH_3$ | H | O |
| 5 | $CH_2$—COOH | H | O |
| 6 | $CH_2$—CO—($NC_4H_8NH$) | H | O |
| 7 | $CH_2$—CO—($NC_4H_8O$) | H | O |
| 8 | $CH_2$—CO—NH($CH_2$—$CH_2$—$NH_2$) | H | O |
| 9 | $CH_2$—CO—NH($CH_3$) | H | O |
| 10 | $CH_2$—CO—N($CH_3$)$_2$ | H | O |
| 11 | $CH_2$—CO—NH($CH_2$—COOH) | H | O |
| 12 | $CH_2$—CO—NH($CH_2$—CO—O—$CH_3$) | H | O |
| 13 | $CH_2$—PO(OH)$_2$ | H | O |
| 14 | $CH_2$—PO(O—$CH_2$—$CH_3$)$_2$ | H | O |
| 15 | $NH_2$ | H | O |
| 16 | NH—CO—$CH_3$ | H | O |
| 17 | NH—CO—$CH_2$—$CH_2$—COOH | H | O |
| 18 | NH—CO—$CH_2$—$NH_2$ | H | O |
| 19 | NH—CO—CH($CH_3$)—$NH_2$ | H | O |
| 20 | NH—$CH_2$—$CH_2$—$NH_2$ | H | O |
| 21 | NH—$CH_2$—$CH_2$—OH | H | O |
| 22 | $SO_2$—($NC_4H_8NH$) | H | O |
| 23 | $SO_2$—($NC_4H_8O$) | H | O |
| 24 | $SO_2$—NH($CH_2$—CO—O—$CH_3$) | H | O |
| 25 | $CH_3$ | H | NOH |
| 26 | $CH_2$—$CH_3$ | H | NOH |
| 27 | $CH(CH_3)_2$ | H | NOH |
| 28 | $NH_2$ | H | NOH |
| 29 | NH—CO—$CH_3$ | H | NOH |
| 30 | NH—CO—$CH_2$—$NH_2$ | H | NOH |

In Table 1, ($NC_4H_8NH$) represents a piperazino group and ($NC_4H_8O$) represents a morpholino group, and $R^1$, $R^2$, $R^5$ and $R^6$–$R^{10}$ represent a hydrogen atom and Y represents an oxygen atom.

Table 2 summarizes the structures of the indirubin compounds of Examples 31 to 69.

TABLE 2

| Example | $R^3$ | $R^4$ | X |
|---|---|---|---|
| 31 | H | H | NO—$CH_2$—$CH_2$—OH |
| 32 | H | H | NO—$CH_2$—$CH_2$—$CH_2$—OH |
| 33 | H | H | NO—$CH_2$—$CH_2$—O—$CH_2$—$CH_2$—OH |
| 34 | H | H | NO—$CH_2$—C(OH)($CH_3$)$_2$ |
| 35 | H | H | NO—$CH_2$—COO$^-$Na$^+$ |
| 36 | H | H | NO—$CH_2$—$CH_2$—COO$^-$Na$^+$ |
| 37 | H | H | NO—$CH_2$—$CH_2$—$CH_2$—COO$^-$Na$^+$ |
| 38 | H | H | NO—$CH_2$—$CH_2$—$CH_2$—$CH_2$—COO$^-$Na$^+$ |
| 39 | H | H | NO—CO—O—$CH_2$—$CH_3$ |
| 40 | H | H | NO—$CH_2$—CO—O—$CH_2$—$CH_3$ |
| 41 | H | H | NO—CO—N($CH_3$)$_2$ |
| 42 | H | H | NO—$CH_2$—CO—$NH_2$ |
| 43 | H | H | NO—$CH_2$—CO—N($CH_3$)$_2$ |
| 44 | H | H | NO—$CH_2$—CO—NH—$CH_2$—COOH |
| 45 | H | H | NO—$CH_2$—$CH_2$—$CH_2$—O-glucose |
| 46 | H | H | NO—$CH_2$—$CH_2$—O-maltose |
| 47 | H | H | NO—$CH_2$—$CH_2$—O-galactose |
| 48 | H | H | NO—$CH_2$—$CH_2$—O-glucose |
| 49 | H | H | NO—$CH_2$—$CH_2$—O-arabinose |
| 50 | H | H | NO—$CH_2$—$CH_2$—Cl |
| 51 | H | H | NO—($CH_2$)$_4$—Cl |
| 52 | H | H | NO—($CH_2$)$_{10}$—Cl |
| 53 | H | H | NO—$CH_2$—$CH_2$—O-glucosamine |
| 54 | H | H | NO—$CH_2$—$CH_2$—O-galactosamine |
| 55 | H | H | NO—$CH_2$—$CH_2$—NH—$CH_2$—(CHOH)$_4$—$CH_2$—OH |
| 56 | H | H | NO—$CH_2$—$CH_2$—NH-(2-deoxy-glucose) |
| 57 | H | H | NO—$CH_2$—$CH_2$—NH-(2-deoxy-galactose) |
| 58 | H | H | NO—$CH_2$—$CH_2$—N($CH_3$)$_2$ |
| 59 | H | H | NO—$CH_2$—$CH_2$—NH—$CH_2$—$CH_2$—OH |
| 60 | H | H | NO—$CH_2$—$CH_2$—N($CH_2$—$CH_2$—OH)$_2$ |
| 61 | H | H | NO—($CH_2$)$_4$—N($CH_2$—$CH_2$—OH)$_2$ |
| 62 | H | H | NO—($CH_2$)$_{10}$—N($CH_2$—$CH_2$—OH)$_2$ |
| 63 | H | H | NO—$CH_2$—$CH_2$—N($CH_2$—$CH_2$)$_2$NH |
| 64 | H | H | NO—$CH_2$—$CH_2$—N($CH_2$—$CH_2$)$_2$O |
| 65 | H | H | NO—$CH_2$—$CH_2$—N($CH_2$—$CH_2$)$_2$N—$CH_3$ |
| 66 | H | H | NO—$CH_2$—$CH_2$—NH—$CH_2$—$CH_2$—NH |
| 67 | $CH_3$ | H | NO—$CH_2$—$CH_2$—OH |
| 68 | $CH_3$ | H | NO—$CH_2$—$CH_2$—O-glucose |
| 69 | $CH_3$ | H | NO—$CH_2$—$CH_2$—NH—$CH_2$—(CHOH)$_4$—$CH_2$—OH |

In Table 2, N($CH_2CH_2$)$_2$NH represents a piperazino group and N($CH_2CH_2$)$_2$O represents a morpholino group, $R^1$–$R^5$ and $R^6$–$R^{10}$ represent a hydrogen atom and Y represents an oxygen atom.

2. Cellular Uptake

Compounds 2, 15, 25, 26, 28, 31, 48 and 55 were examined with respect to their uptake by LXFL-529L cells. Results are shown in Table 3. The amounts of the substances which were taken up by the cells are given depending on the concentration of the substance within the incubation medium. The time of incubation was 2 hours in all of the experiments. Furthermore, distribution between cytosol and the cellular organelles (particular) was measured and is given in the last two columns of Table 3.

TABLE 3

| Compound | concentration of incubation [μM] | amount taken up [μg/mg protein] | distribution cytosol [%] | distribution particular [%] |
|---|---|---|---|---|
| 2 | 10 | 0.20 ± 0.05 | 10 ± 2 | 90 ± 6 |
|   | 20 | 0.22 ± 0.07 | 5 ± 2 | 95 ± 3 |
| 15 | 10 | 0.25 ± 0.04 | 15 ± 2 | 85 ± 4 |
|   | 20 | 0.29 ± 0.05 | 6 ± 1 | 94 ± 4 |
| 25 | 10 | 0.12 ± 0.03 | 20 ± 4 | 80 ± 5 |
|   | 20 | 0.15 ± 0.04 | 16 ± 3 | 84 ± 4 |
|   | 50 | 0.18 ± 0.06 | 10 ± 4 | 90 ± 8 |
| 26 | 10 | 0.10 ± 0.03 | 18 ± 3 | 82 ± 6 |
|   | 20 | 0.13 ± 0.05 | 11 ± 3 | 89 ± 5 |
| 28 | 10 | 0.20 ± 0.06 | 10 ± 2 | 90 ± 6 |
|   | 20 | 0.23 ± 0.05 | 90 ± 6 | 94 ± 5 |
| 31 | 10 | 0.27 ± 0.06 | 7 ± 1 | 93 ± 7 |
|   | 20 | 0.31 ± 0.07 | 7 ± 2 | 93 ± 6 |
| 48 | 10 | 0.20 ± 0.05 | 13 ± 3 | 87 ± 7 |
|   | 20 | 0.25 ± 0.04 | 5 ± 1 | 95 ± 6 |
| 55 | 10 | 0.37 ± 0.07 | 9 ± 2 | 91 ± 5 |
|   | 20 | 0.42 ± 0.06 | 7 ± 1 | 93 ± 6 |

3. Evaluation of Tumor Cell Growth Inhibition

Examples 1–49 and 53–69 were tested with respect to their anti-tumor activity via a standard cellular growth inhibition assay (SRB-assay) using cells of the large-cell lung carcinoma of the tumor line LXFL-529L and cells of the mammary carcinoma cell line MCF-7. The results are shown in Table 4. Tumor cell growth inhibition was determined by the sulfo-rhodamine B-assay (SRB-assay) according to Skehan et al. (1990), *J. Natl. Cancer Institute* 82, pages 1107–1112. Incubation was for three days in serum-containing medium. Results are given as $IC_{50}$-values defined as the concentration of compound [μM] inducing 50% growth inhibition, compared to vehicle treated control.

TABLE 4

| Example | SRB-Assay $IC_{50}$ [μM] LXFL-529L | MCF-7 |
|---|---|---|
| 1 (6-iodo-indirubin) | 15.0 ± 0.5 | 15.0 ± 0.8 |
| 2 (5-ethyl-indirubin) | 7.0 ± 0.2 | 7.0 ± 0.2 |
| 3 (5-isopropyl-indirubin) | 4.0 ± 0.2 | 0.5 ± 0.2 |
| 4 (5-n-propyl-indirubin) | 7.0 ± 0.4 | 6.5 ± 0.5 |
| 5 (5-(carboxymethyl)-indirubin) | 18.0 ± 1.0 | 19.5 ± 1.4 |
| 6 (5-[2-(piperazin-1-yl)-ethan-2-one-1-yl]-indirubin) | 4.0 ± 0.5 | 8.0 ± 0.9 |
| 7 (5-[2-(morpholin-4-yl)-ethan-2-one-1-yl]-indirubin) | 5.5 ± 0.7 | 7.5 ± 0.6 |
| 8 (N-(2-amino-ethyl)-2-[3-(3'-oxo-(2'H3'H)indol-2'-ylidene)-(2H3H)indol-2-one-5-yl]-acetamide) | 3.5 ± 0.7 | 4.0 ± 0.6 |
| 9 (N-methyl-2-[3-(3'-oxo-(2'H3'H)indol-2'-ylidene)-(2H3H)indol-2-one-5-yl]-acetamide) | 11.5 ± 0.6 | 17.0 ± 1.0 |
| 10 (N,N-dimethyl-2-[3-(3'-oxo-(2'H3'H)indol-2'-ylidene)-(2H3H)indol-2-one-5-yl]-acetamide) | 16.0 ± 0.9 | 20.0 ± 1.3 |
| 11 (2-{2-[3-(3'-oxo-(2'H3'-H)indol-2'-ylidene)-(2H3H)indol-2-one-5-yl]-acetylamino}-acetic acid) | 15.0 ± 0.8 | 20.5 ± 0.6 |
| 12 (methyl-2-{2-[3-(3'-oxo-(2'H3'H)indol-2'-ylidene)-(2H3H)indol-2-one-5-yl]-acetylamino}-acetate) | 8.0 ± 0.8 | 6.5 ± 1.2 |
| 13 ([3-(3'-oxo-(2'H3'H)indol-2'-ylidene)-(2H3H)indol-2-one-5-yl]-methyl-phosphonic acid) | 8.5 ± 0.8 | 6.5 ± 1.0 |
| 14 (diethyl-{[3-(3'-oxo-(2'H3'H)indol-2'-ylidene)-(2H3H)indol-2-one-5-yl]-methyl}-phosphonate) | 6.5 ± 1.2 | 6.0 ± 1.1 |
| 15 (5-amino-indirubin) | 8.0 ± 0.7 | 5.0 ± 0.5 |
| 16 (5-acetylamino-indirubin) | 10.0 ± 0.8 | 15.0 ± 1.0 |
| 17 ([3-(3'-oxo-(2'H3'H)indol-2'-ylidene)-(2H3H)indol-2-one-5-yl]-succinamic acid) | 12.5 ± 0.7 | 14.0 ± 0.9 |
| 18 (2-amino-N-[3-(3'-oxo-(2'H3'H)indol-2'-ylidene)-(2H3H)indol-2-one-5-yl]-acetamide) | 4.0 ± 0.4 | 3.0 ± 0.3 |
| 19 (2-amino-N-[3-(3'-oxo-(2'H3'H)indol-2'-ylidene)-(2H3H)indol-2-one-5-yl]-propionamide) | 7.0 ± 0.7 | 5.0 ± 0.6 |
| 20 (5-(2-amino-ethyl)-amino-indirubin) | 4.0 ± 0.3 | 3.5 ± 0.4 |
| 21 (5-(2-hydroxy-ethyl)-amino-indirubin) | 3.0 ± 0.5 | 5.0 ± 0.6 |
| 22 (indirubin-5-sulfonic acid-(piperazin-1-yl-amide)) | 3.0 ± 0.5 | 2.0 ± 0.3 |
| 23 (indirubin-5-sulfonic acid-(morpholin-4-yl-amide)) | 4.5 ± 0.8 | 3.0 ± 0.9 |
| 24 (methyl-2-{[3-(3'-oxo-(2'H3'H)indol-2'-ylidene)-(2H3H)indol-2-one-5-yl]-sulfonylamino}-acetate) | 16.0 ± 0.8 | 25.0 ± 0.9 |
| 25 (5-methyl-indirubin-3'-monooxime) | 6.0 ± 0.8 | 6.0 ± 0.9 |
| 26 (5-ethyl-indirubin-3'-monooxime) | 6.0 ± 0.6 | 7.0 ± 0.9 |
| 27 (5-isopropyl-indirubin-3'-monooxime) | 5.5 ± 0.6 | 5.0 ± 0.9 |
| 28 (5-amino-indirubin-3'-monooxime) | 7.5 ± 0.4 | 5.0 ± 0.8 |
| 29 (5-acetylamino-indirubin-3'-monooxime) | 4.0 ± 0.9 | 5.0 ± 0.5 |
| 30 (2-amino-N-[3-(3'-hydroxyimino-(2'H3'H)indol-2'-ylidene)-(2H3H)indol-2-one-5-yl]-acetamide) | 6.0 ± 0.8 | 6.0 ± 0.7 |
| 31 (3-[3'-(iminooxy-O-(2-hydroxy-ethyl)-(2'H3'H)indol-2'-ylidene]-(2H3H)indol-2-one) | 1.5 ± 0.4 | 2.5 ± 0.4 |
| 32 (3-[3'-(iminooxy-O-(3-hydroxy-propyl)-(2'H3'H)indol-2'-ylidene]-(2H3H)indol-2-one) | 1.5 ± 0.3 | 2.0 ± 0.4 |
| 33 (3-{3'-[iminooxy-O-(2-(2-hydroxy-ethoxy)-ethyl)]-(2'H3'H)indol-2'-ylidene}-(2H3H)indol-2-one) | 2.0 ± 0.4 | 2.5 ± 0.5 |
| 34 (3-{3'-[iminooxy-O-((2-hydroxy-2-methyl)-propyl)]-(2'H3'H)indol-2'-ylidene}-(2H3H)indol-2-one) | 2.0 ± 0.5 | 2.0 ± 0.3 |
| 35 (2-{O-[2'-(2-oxo-(2H3H)indol-3-ylidene)-(2'H3'H)indol-3'-ylidene]-aminooxy}-acetic acid (sodium salt)) | 15.0 ± 0.8 | 20.5 ± 0.9 |
| 36 (3-{O-[2'-(2-oxo-(2H3H)indol-3-ylidene)-(2'H3'H)indol-3'-ylidene]-aminooxy}-propionic acid (sodium salt)) | 15.0 ± 0.8 | 16.0 ± 0.7 |
| 37 (4-{O-[2'-(2-oxo-(2H3H)indol-3-ylidene)-(2'H3'H)indol-3'-ylidene]-aminooxy}-butyric acid (sodium salt)) | 12.0 ± 1.0 | 14.0 ± 1.1 |
| 38 (5-{O-[2'-(2-oxo-(2H3H)indol-3-ylidene)-(2'H3'H)indol-3'-ylidene]-aminooxy}-pentanoic acid (sodium salt)) | 14.0 ± 0.8 | 14.0 ± 0.7 |
| 39 (3-[3'-(iminooxy-O-carbethoxy)-(2'H3'H)indol-2'-ylidene]-(2H3H)indol-2-one) | 4.5 ± 0.7 | 10.0 ± 0.9 |
| 40 (ethyl-2-{O-[2'-(2-oxo-(2H3H)indol-3-ylidene)-(2'H3'H)indol-3'-ylidene]-aminooxy}-acetate) | 6.0 ± 0.4 | 10.0 ± 0.7 |
| 41 (3-{3'-[iminooxy-O-((N,N)-dimethyl-carbamoyl)]-(2'H3'H)indol-2'-ylidene}-(2H3H)indol-2-one) | 5.0 ± 0.6 | 7.5 ± 0.9 |
| 42 (2-{O-[2'-(2-oxo-(2H3H)indol-3-ylidene)-(2'H3'H)indol-3'-ylidene]-aminooxy}-acetamide) | 2.0 ± 0.3 | 6.0 ± 0.5 |
| 43 (N,N-dimethyl-2-{O-[2'-(2-oxo-(2H3H)indol-3-ylidene)-(2'H3'H)indol-3'-ylidene]-aminooxy}-acetamide) | 7.0 ± 1.1 | 9.2 ± 0.9 |
| 44 (2-{2-[O-(2'-(2-oxo-(2H3H)indol-3-ylidene)-(2'H3'H)indol-3'-ylidene)-aminooxy]-acetylamino}-acetic acid) | 20.0 ± 0.8 | 18.0 ± 1.3 |
| 45 (3-{3'-[iminooxy-O-(3-D-glucopyranosylpropyl)]-(2'H3'H)indol-2'-ylidene}-(2H3H)ifldOl-2-one) | 19.0 ± 0.9 | 10.5 ± 0.6 |

TABLE 4-continued

| | SRB-Assay IC$_{50}$ [μM] | |
|---|---|---|
| Example | LXFL-529L | MCF-7 |
| 46 (3-{3'-[iminooxy-O-(O$^4$-α-D-glucopyranosyl-2-D-glucopyranosylethyl)]-(2'H3'H)indol-2'-ylidene}-(2H3H)indol-2-one) | 24.0 ± 1.3 | 7.0 ± 0.9 |
| 47 (3-{3'-[iminooxy-O-(2-D-galactopyranosylethyl)]-(2'H3'H)indol-2'-ylidene}-(2H3H)indol-2-one) | 17.0 ± 1.2 | 9.5 ± 0.9 |
| 48 (3-{3'-[iminooxy-O-(2-D-glucopyranosylethyl)]-(2'H3'H)indol-2'-ylidene}-(2H3H)indol-2-one) | 21.0 ± 1.5 | 3.5 ± 0.6 |
| 49 (3-{3'-[iminooxy-O-(2-L-arabinopyranosylethyl)]-(2'H3'H)indol-2'-ylidene}-(2H3H)indol-2-one) | 20.5 ± 1.4 | 5.0 ± 0.7 |
| 53 (3-{3'-[iminooxy-O-(2-(2-amino-2-deoxy-D-glucopyranosyl)-ethyl)]-(2'H3'H)indol-2'-ylidene}-(2H3H)indol-2-one) | 15.0 ± 0.9 | 7.0 ± 0.7 |
| 54 (3-{3'-[iminooxy-O-(2-(2-amino-2-deoxy-D-galactopyranosyl)-ethyl)]-(2'H3'H)indol-2'-ylidene}-(2H3H)indol-2-one) | 16.0 ± 1.1 | 9.0 ± 0.9 |
| 55 (3-{3'-[iminooxy-O-(N-(1-deoxy-glucitol)-2-amino-ethyl)]-(2'H3'H)indol-2'-ylidene}-(2H3H)indol-2-one) | 3.0 ± 0.6 | 3.0 ± 0.8 |
| 56 (3'-{3-[iminooxy-O-(N-(2-deoxy-glucose)-2-amino-ethyl)]-(2'H3'H)indol-2'-ylidene}-(2H3H)indol-2-one) | 12.0 ± 1.3 | 14.0 ± 1.2 |
| 57 (3-{3'-[iminooxy-O-(N-(2-deoxy-galactose)-2-amino-ethyl)]-(2'H3'H)indol-2'-ylidene}-(2H3H)indol-2-one) | 23.0 ± 1.4 | 20.5 ± 1.6 |
| 58 (3-{3'-[iminooxy-O-((N,N)-dimethyl-2-amino-ethyl)]-(2'H3'H)indol-2'-ylidene}-(2H3H)indol-2-one) | 5.0 ± 0.9 | 6.5 ± 1.1 |
| 59 (3-{3'-[iminooxy-O-(N-hydroxyethyl-2-amino-ethyl)]-(2'H3'H)indol-2'-ylidene}-(2H3H)indol-2-one) | 11.6 ± 0.8 | 13.6 ± 1.2 |
| 60 (3-{3'-[iminooxy-O-((N,N)-bis(hydroxyethyl)-2-amino-ethyl)]-(2'H3'H)indol-2'-ylidene}-(2H3H)indol-2-one) | 3.0 ± 0.4 | 4.5 ± 0.5 |
| 61 (3-{3'-[iminooxy-O-((N,N)-bis(hydroxyethyl)-4-amino-butyl)]-(2'H3'H)indol-2'-ylidene}-(2H3H)indol-2-one) | 8.0 ± 0.3 | 12.4 ± 0.7 |
| 62 (3-{3'-[iminooxy-O-((N,N)-bis(hydroxyethyl)-10-amino-decyl)]-(2'H3'H)indol-2'-ylidene}-(2H3H)indol-2-one) | 14.0 ± 1.0 | 13.5 ± 1.3 |
| 63 (3-{3'-[iminooxy-O-(2-(piperazin-1-yl)-ethyl)]-(2'H3'H)indol-2-ylidene}-(2H3H)indol-2-one) | 8.0 ± 0.6 | 9.5 ± 0.8 |
| 64 (3-{3'-[iminooxy-O-(2-(morpholin-4-yl)-ethyl)]-(2'H3'H)indol-2-ylidene}-(2H3H)indol-2-one) | 10.0 ± 0.6 | 9.0 ± 1.2 |
| 65 (3-{3'-[iminooxy-O-(2-(4-methyl-piperazin-1-yl)-ethyl)]-(2'H3'H)indol-2'-ylidene}-(2H3H)indol-2-one) | 6.5.0 ± 0.6 | 7.5 ± 0.8 |
| 66 (3-{3'-[iminooxy-O-(2-(2-amino-ethyl)-amino-ethyl)]-(2'H3'H)indol-2'-ylidene}-(2H3H)indol-2-one) | 7.0 ± 0.6 | 8.0 ± 1.2 |
| 67 (3-[3'-[iminooxy-O-(2-hydroxy-ethyl)]-(2H'3H')indol-2'-ylidene]-5-methyl-(2H3H)indol-2-one) | 1.0 ± 0.5 | 1.5 ± 0.6 |
| 68 (3-[3'-[iminooxy-O-(2-D-glucopyranosylethyl)]-(2H'3H')indol-2'-ylidene]-5-methyl-(2H3H)indol-2-one) | 17.0 ± 0.8 | 2.5 ± 0.8 |
| 69 (3-[3'-[iminooxy-O-(N-(1-deoxy-glucitol)-2-amino-ethyl)]-(2H'3H')indol-2'-ylidene]-5-methyl-(2H3H)indol-2-one) | 3.5 ± 0.7 | 2.5 ± 0.9 |

What is claimed is:

1. Cell membrane penetrating indirubin derivative having the general formula (I):

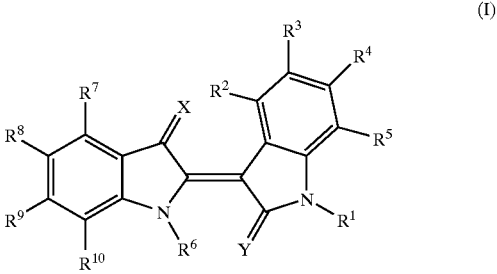

wherein

Y is O, and

X represents a group N—A—B—R$^{14}$ in which
A represents an oxygen atom,
B represents a group $[(CD_2)_nZ]_m$ wherein
D represents a hydrogen atom, a straight chain or branched-chain alkyl group having 1 to 18 carbon atoms which can additionally carry one or more hydroxy and/or amino groups,
Z is an oxygen atom or —NH—,
n is an integer and m is an integer, wherein n and m are not 0,
the group R$^{14}$ represents a hydrogen atom, a straight-chain or branched-chain alkyl group having 1 to 18 carbon atoms which can carry one or more hydroxy groups and/or amino groups, a substituted or unsubstituted aryl group, which can comprise one or more heteroatoms, an aralkyl group or a glycoside selected from monosaccharides, disaccharides or oligosaccharides, or a derivative of the glycoside, R$^2$, R$^3$, R$^4$, R$^5$, R$^7$, R$^8$, R$^9$ and R$^{10}$ can be the same or different and represent a hydrogen atom; a halogen atom; a hydroxy group; a nitroso group; a nitro group; an aryloxy group; an alkoxy group; a straight-chain or branched-chain alkyl group having 1 to 18 carbon atoms which can additionally carry one or more hydroxy and/or amino groups; a cycloalkyl group having 3 to 7 carbon atoms which can comprise one or more heteroatoms; a substituted or unsubstituted aryl group which can comprise one or more heteroatoms; an aralkyl group; a trifluoromethyl group; a —COOM group; a —CH$_2$COOM group, wherein M is hydrogen, a straight-chain or branched-chain alkyl group having 1 to 18 carbon atoms which can additionally carry one or more hydroxy and/or amino groups; a NR$^{11}$R$^{12}$ group, or a SO$_2$NR$^{11}$R$^{12}$ group, wherein R$^{11}$ and R$^{12}$ can be the same or different and represent a hydrogen atom, a straight-chain or branched-chain alkyl group having 1 to 18 carbon atoms which can additionally carry one or more hydroxy and/or amino groups, and R$^1$ and R$^6$ each represents a hydrogen atom.

2. The cell membrane penetrating indirubin derivative according to claim 1, wherein in the group $[(CD_2)_nZ]_m$, n represents 2 or 3, and m represents 1 or 2.

3. Indirubin derivative according to claim 1, wherein the compound having the general formula (I) is bound to a polyethyleneglycolester or a polyethyleneglycolether.

4. Indigoid bisindole derivative which is (3-[3'-(Iminooxy-O-(2-hydroxy-ethyl)-(2'H3'H)indol-2'-ylidene]-(2H3H)indol-2-one), (3-[3'-(Iminooxy-O-(3-hydroxy-propyl)-(2'H3'H)indol-2'-ylidene]-(2H3H)indol-2-one), (3-{3'-[Iminooxy-O-(2-(2-hydroxy-2-ethoxy)-ethyl)]-(2'H3'H)indol-2'-ylidene}-(2H3H)indol-2-one, (3-{3'-[Iminooxy-O-((2-hydroxy-2-methyl)-propyl)]-(2'H3'H)indol-2'-ylidene}-(2H3H)indol-2-one), (3-{3'-[Iminooxy-O-(3-D-glucopyranosylpropyl)]-(2'H3'H)indol-2'-ylidene}-(2H3H)indol-2-one), (3-{3'-[Iminooxy-O-($O^4$-α-D-glucopyranosyl-2-D-glucopyranosylethyl)]-(2'H3'H)indol-2'-ylidene}-(2H3H)indol-2-one), (3-{3'-[Iminooxy-O-(2-D-galactopyranosylethyl)]-(2'H3'H)indol-2'-ylidene}-(2H3H)indol-2-one), (3-{3'-[Iminooxy-O-(2-D-glucopyranosylethyl)]-(2'H3'H)indol-2'-ylidene}-(2H3H)indol-2-one), (3-{3'-[Iminooxy-O-(2-L-arabinopyranosylethyl)]-(2'H3'H)indol-2'-ylidene}-(2H3H)indol-2-one), (3-{3'-[Iminooxy-O-(2-(2-amino-2-deoxy-D-glucopyranosyl)-ethyl)]-(2'H3'H)indol-2'-ylidene}-(2H3H)indol-2-one), (3-{3'-[Iminooxy-O-(2-(2-amino-2-deoxy-D-galactopyranosyl)-ethyl)]-(2'H3'H)indol-2'-ylidene}-(2H3H)indol-2-one), (3-{3'-[Iminooxy-O-(N-(1-deoxy-glucitol)-2-aminoethyl)]-(2'H3'H)indol-2'-ylidene}-(2H3H)indol-2-one), (3-{3'-[Iminooxy-O-(N-(2-deoxy-glucose)-2-aminoethyl)]-(2'H3'H)indol-2'-ylidene}-(2H3H)indol-2-one), (3-{3'-[Iminooxy-O-(N-(2-deoxy-galactose)-2-aminoethyl)]-(2'H3'H)indol-2'-ylidene}-(2H3H)indol-2-one), (3-{3'-[Iminooxy-O-(N-hydroxyethyl-2-amino-ethyl)]-(2'H3'H)indol-2'-ylidene}-(2H3H)indol-2-one), (3-{3'-[Iminooxy-O-(2-(2-amino-ethyl)-amino-ethyl)]-(2'H3'H)indol-2'-ylidene}-(2H3H)indol-2-one), (3-[3'-[Iminooxy-O-(2-hydroxy-ethyl)]-(2H'3H')indol-2'-ylidene]-5-methyl(2H3H)indol-2-one), (3-[3'-[Iminooxy-O-(2-D-glucopyranosylethyl)]-(2H'3H')indol-2'-ylidene]-5-methyl-( 2H3H)indol-2-one) or (3-[3'-[Iminooxy-O—(N-(1-deoxy-glucitol)-2-aminoethyl)]-(2H'3H')indol-2'-ylidene]-5-methyl-(2H3H)indol-2-one).

5. Indirubin derivative according to claim 1, wherein the indirubin derivative is in the form of a physiologically acceptable salt.

6. Pharmaceutical formulation comprising at least one indirubin derivative according to claim 1.

7. Method for the manufacture of a medicament for the treatment of human solid tumors comprising preparing a pharmaceutical formulation according to claim 6.

8. Indirubin derivative according to claim 3, wherein the indirubin derivative is in the form of a physiologically acceptable salt.

9. Indigoid bisindole derivative according to claim 4, wherein the indigoid bisindole derivative is in the form of a physiologically acceptable salt.

10. Pharmaceutical formulation comprising at least one indirubin derivative according to claim 3.

11. Pharmaceutical formulation comprising at least one of the indigoid bisindole compounds according to claim 4.

12. Pharmaceutical formulation comprising at least one indirubin derivative according to claim 5.

13. Pharmaceutical formulation comprising at least one indirubin derivative according to claim 8.

14. Pharmaceutical formulation comprising at least one indirubin derivative according to claim 9.

* * * * *